United States Patent [19]

Keller

[11] Plant 5,239

[45] May 29, 1984

[54] DISTINCT VARIETY OF STREPTOCARPUS NAMED KATHI

[75] Inventor: Emil Keller, Hedingen, Switzerland

[73] Assignee: Oglevee Associates, Inc., Connellsville, Pa.

[21] Appl. No.: 452,859

[22] Filed: Dec. 28, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus is characterized by its tight distinct bouquet, small flowers and large number of flowers.

1 Drawing Figure

BACKGROUND OF THE NEW PLANT

The present invention comprises a new and distinct cultivar of *Streptocarpus* × *hybridus* known by the varietal name of Kathi. The new cultivar was developed in a breeding program and is a cross of the varieties Mary (pollen parent) and Gloria Hellrosa (seed parent). The new cultivar is distinguished from its parentage by its new color and big yellow throat area. It is similar to its parentage in that it has well developed flowers and big leaves.

The new cultivar can also be compared with the Streptocarpus known by the varietal name Marna (U.S. Plant Pat. No. 4,524). The new cultivar has less foliage and lays flatter than Marna. In addition, the flower stems raise into a tight distinct bouquet with more flowers and smaller flowers as compared to Marna.

The new cultivar was discovered through a breeding program in 1979 in Hedingen, Switzerland; was first asexually reproduced by cuttings in Hedingen, Switzerland; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of eight weeks. This response time is measured from a plantlet which is a well rooted young plant in a five centimeter pot to a flowering plant in a fifteen centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken outdoors using natural sunlight. Color references are primarily to the R.H.S. color chart of The Royal Horticultural Society of London. Some color reference is to Exotica III and such reference is duly noted.

Botanical classification: Gesneriaceae (family); *Streptocarpus* × *hybridus* (genus × species).

Flower:

*Fully expanded.*—5.5 centimeters.

*Borne.*—In clusters of two to seven flowers per flower stalk above the foliage. Flower stalks arise close together and initiate at base of leaf.

*Stems.*—Single, long and pubescent.

*Form.*—Funnel formed in an umbel.

*Permanence.*—Long lasting 21 to 25 days.

Color:

*Tonality from a distance.*—Grape violet with mimosa throat (Exotica III).

*Front of petals.*—Young flowers Fan 2 Violet Group 88-A, older flowers Fan 2 Blue Group 89-C. Dark veining Fan 2 Red Purple Group 89-A.

*Throat.*—Fan 1 Yellow Group 3-C, some of the veining from petals extend into throat.

*Reverse of petals.*—Fan 2 Red Purple Group 88-C.

*Discoloration.*—Older blooms tend to include more blue.

Petals:

*Texture.*—Velvet.

*Appearance.*—Individually lobed and slightly cuneate.

*Arrangement.*—Regularly united into an elliptical form.

*Persistence.*—Lives for 21 to 25 days and remains on plant in dry form until picked.

*Fragrance.*—None.

Reproductive organs:

*Anthers.*—Two per flower and interconnected.

*Filament.*—0.6 Centimeter and attaches to petal about 3 centimeters up from base.

*Pollen.*—Generally nonfertile.

*Style.*—Has a purplish cast and extends 0.7 centimeter from tip of ovary to a flattened stigma.

*Ovaries.*—Includes purple streaks, long and narrow and 1 centimeter long and 1.5 millimeter in diameter.

Plant:

*Form.*—Leaves rosette from a crown at the soil line.

*Growth.*—A spreading, free flowing habit.

*Height from soil line.*—20 to 23 centimeters.

*Spread.*—35 to 45 centimeters.

Foliage:

*Top side.*—Fan 3 Green Group 137-B.

*Under side.*—Fan 4 Greyed Green Group 193-B.
*Size.*—15 to 30 centimeters long and 4 to 8 centimeters wide at the widest point.
*Quantity.*—5 to 7 leaves.
*Shape.*—Oblanceolate.
*Ribs and veins.*—Pinnate.
*Rib and vein color.*—Fan 3 Green Group 139-D,

*Margin.*—Cuneate.
*Leaf tips.*—Obtuse.
*Leaf base.*—Attenuate.

I claim:

1. A new and distinct variety of Streptocarpus substantially as herein shown and described.

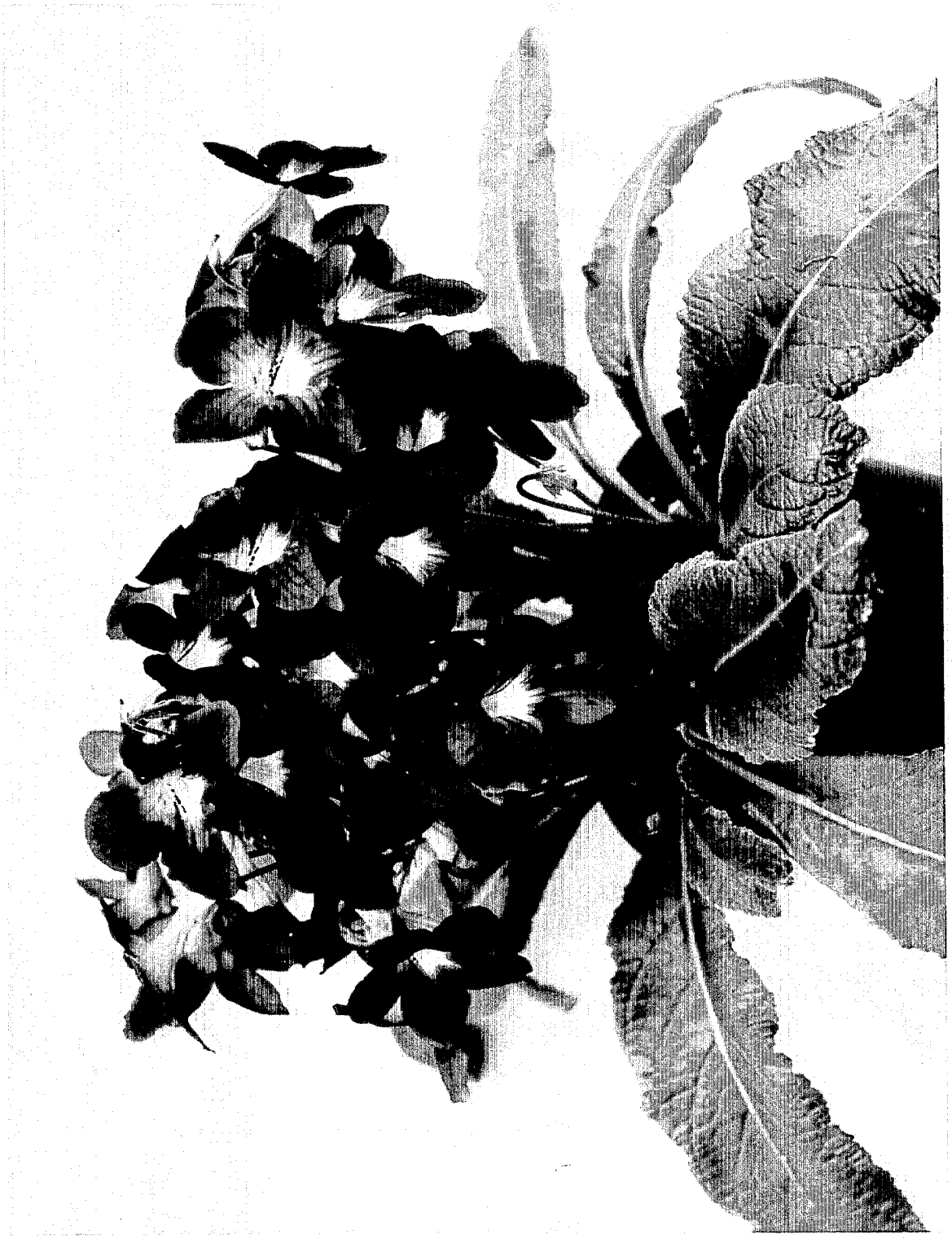

* * * * *